United States Patent [19]

Wardlaw et al.

[11] Patent Number: 5,251,474
[45] Date of Patent: Oct. 12, 1993

[54] CENTRIFUGED MATERIAL LAYER MEASUREMENT IN AN EVACUATED TUBE

[76] Inventors: Stephen C. Wardlaw, 191 N. Cove Rd., Old Saybrook, Conn. 06475; Robert A. Levine, 31 Pilgrim La., Guilford, Conn. 06437

[21] Appl. No.: 822,321
[22] Filed: Jan. 16, 1992
[51] Int. Cl.$^5$ .................. G01N 33/48; B04B 5/04; B01D 21/26; B01D 17/038
[52] U.S. Cl. .................. 73/61.41; 73/61.71; 73/61.44; 210/789
[58] Field of Search .......... 73/64.41, 61.41, 61.71; 210/789

[56] References Cited

U.S. PATENT DOCUMENTS

| | | | |
|---|---|---|---|
| 3,202,483 | 8/1965 | McKeon et al. | 73/61.41 |
| 3,814,248 | 6/1974 | Lawhead | 210/789 |
| 3,897,343 | 7/1975 | Ayres | 210/789 |
| 4,055,501 | 10/1977 | Cornell | 210/789 |
| 4,088,582 | 5/1978 | Murty et al. | 210/789 |
| 4,091,659 | 5/1978 | Massey et al. | 73/61.63 |
| 4,152,269 | 5/1979 | Babson | 210/789 |
| 4,152,270 | 5/1979 | Cornell | 210/789 |
| 4,154,690 | 5/1979 | Ballies | 210/789 |
| 4,202,769 | 5/1980 | Greenspan | 210/789 |
| 4,579,828 | 4/1986 | Ali | 73/64.41 |
| 4,953,975 | 9/1990 | Levine et al. | 73/61.44 |

FOREIGN PATENT DOCUMENTS 8701457  3/1987  World Int. Prop. O. .......... 210/789

Primary Examiner—Hezron E. Williams
Assistant Examiner—George Dombroske
Attorney, Agent, or Firm—William W. Jones

[57] ABSTRACT

Centrifuged material layer measurements are made in an evacuated glass or clear plastic tube which contains a float. When possibly contaminated materials, such as blood, are being tested the use of the evacuated tube allows the measurements to be made without the technician being exposed to the blood. The tubes are large enough to hold approximately one ml of blood, and are filled with an inert gas at low pressure. The floats are formed with a through passage into which the cell bands to be expanded will settle during centrifugation.

13 Claims, 1 Drawing Sheet

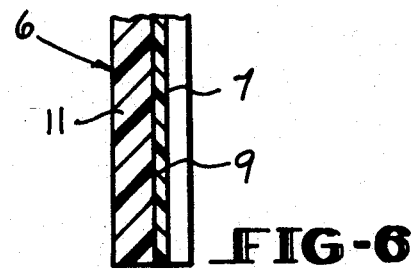
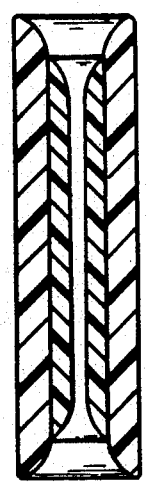
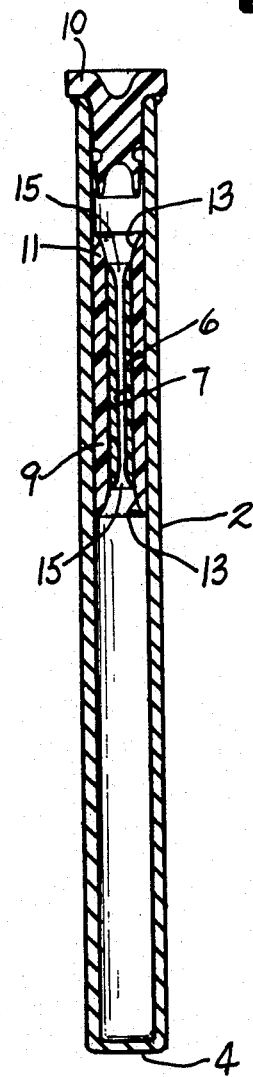
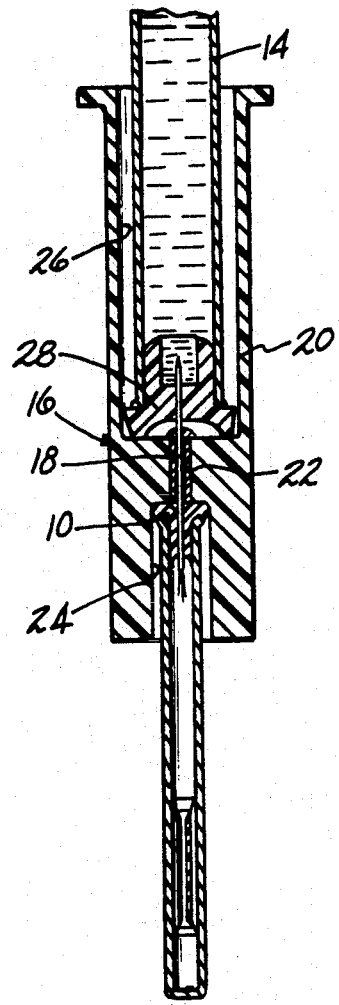
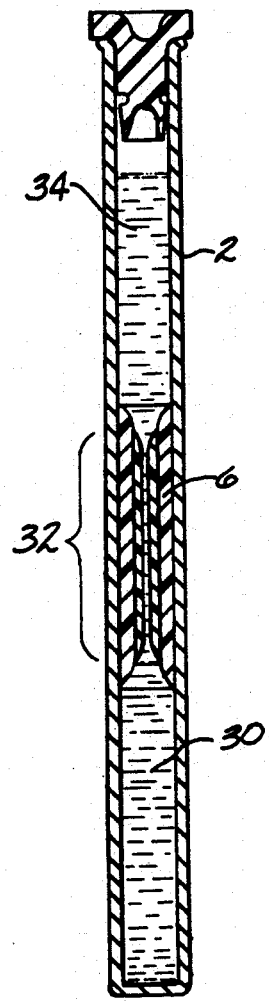

CENTRIFUGED MATERIAL LAYER MEASUREMENT IN AN EVACUATED TUBE

This invention relates to paraphernalia for determining material layer volume values in a centrifuged sample of a material such as blood. The tests are performed in an evacuated tube containing a float which expands the layers being measured.

A technique has been developed to measure constituent layers in a complex material mixture by centrifuging a sample of the material mixture in a capillary or other tube which contains a float. The float is preferably cylindrical and of a specific gravity which causes it to settle into the centrifuged mixture to a degree which creates a free volume annulus in the tube into which the layer, or layers to be measured will settle. The layers to be measured are thus physically elongated, and can be more easily and accurately measured. This technique is described in U.S. Pat. Nos. 4,027,660, issued Jun. 7, 1977; 4,082,085 issued Apr. 4, 1978; 4,156,570 issued May 29, 1979; and others. U.S. Pat. No. 4,091,659, issued May 30, 1978 discloses a slotted float which provides a flow channel for plasma in the blood sample during centrifugation to minimize cell band disruption in the annulus.

When the material being tested is a possibly contaminated material such as blood, it is desirable to make provisions for protecting the technician against exposure to the blood. When the aforesaid prior art techniques are performed with capillary tubes, the person performing the test is exposed to the blood since the capillary tubes are open-ended. Thus, despite taking normal precautions in handling of the samples, the chance of being contaminated by a blood sample exists.

This invention is directed to paraphernalia for use in the collecting and testing of a possibly contaminated material such as blood, wherein the person doing the testing is never exposed to the blood. Thus, the possibility of becoming infected by a contaminated blood sample is eliminated. When the tube and float of this invention are used, the blood sample is collected and tested in a sealed tube, and the blood never leaves the confines of the tube after it is collected. An additional advantage of the invention resides in the fact that it entails the use of a unitary sealed tube which contains all of the required components for use in performing the cell counts, and those components are disposed in a stable, inert environment. The tube used in this invention is preferably a glass tube with an integral closed end. It will be the same length as a capillary tube but will have a larger diameter so as to be able to contain about 0.9 ml of blood. A cylindrical float is disposed inside of the tube, which float has an accurately controlled outside diameter so as to fit snugly in the tube bore under static conditions. The float is formed with a longitudinal through channel which receives and expands the white cell and platelet layers in the blood sample after centrifugation thereof. The float is made from a plastic material having a specific gravity that causes it to float in the packed red cells after centrifugation of the blood sample in the tube. The required reagents such as a stain and a red cell densifier, preferably potassium oxalate, are disposed in the tube, preferably in liquid form. An elastomeric stopper closes the open end of the tube, and the interior of the tube is filled with an inert gas at low pressure. The low pressure in the tube is used to draw the blood sample into the tube, preferably from a primary blood collection device, such as that sold by Becton Dickinson and Company under the trademark "Vacutainer".

The float is preferably a compound structure made from plastics which have a specific gravity which causes the float to be buoyed up in the centrifuged red cell layer. The float is formed with a first stable portion which has the through channel, and a second sleeve portion which will expand and contract responsive to the magnitude of dynamic forces imposed on the float during performance of the sample centrifugation. The float first portion is preferably formed from a plastic material, such as a transparent styrene, which is dimensionally stable during centrifugation. The second portion of the float which surrounds the first portion can be formed from a transparent pliable vinyl plastic. The two components of the float can be joined together by coextruding or by co-molding the float components. The tube can be provided with a lubricant coating, such as a silicone coating to enhance movement of the float in the tube during centrifugation. Specific plastics which can be used for the first and second portions of the float are polystyrene and polyvinylchloride (PVC) respectively.

The primary blood collection tube will be provided with a needle which is used to pierce the elastomeric stopper in the tube of this invention, whereupon the blood will flow from the collection tube, through the needle, into the testing tube.

When the larger bore diameter tube and the larger float with an axial bore are used per this invention, there occurs a relaxation in the diameter dimensional tolerances in the tube bore ID. It is desirable to achieve a ten fold expansion of the white cell and platelet layers when performing the cell count measurements with the tube-float combination of the aforesaid prior art. When using the enlarged tubes and floats of this invention, the ten fold expansion can be obtained from a through channel diameter of 1.265 mm when a 4.0 mm diameter tube bore is used. This compares with a free space of about 43 microns with the prior art capillary tubes and floats. The $+/-$ variations in the bore diameter is 20 microns when using the paraphernalia of this invention.

Another benefit deriving from the use of the larger tube and float paraphernalia is the improvement in the hydrodynamics of the centrifugation. After blood is added to the tube, the tube is centrifuged at 10,000 G, as is the usual practice. With a float of this type; several forces are brought into play. First, the centripedal acceleration forces the float to the end of the tube at the same time as the blood cells are separating. Secondly, a tidal force is exerted on the float because the acceleration is unequal at the ends of the float. This tidal force is about 2,000 G at near the center of the tube. This exerts a stretching or contracting force on the float of about 500 G, which is enough to sufficiently elongate the pliable elastomeric portion of the float and slightly decrease its diameter, allowing it to easily slip down the tube. As the float settles into the RBC layer, the buoyant forces overcome the tidal forces, and the float relaxes to its normal diameter, and it comes into close approximation to the walls of the tube.

The cells and components of the buffy coat layer are expanded linearly in the narrow bore channel in the float and can be measured as before. Another significant advantage of this configuration is that the hydrodynamics are nearly ideal as compared to the situation when the cells are expanded into an annular free space.

It is therefore an object of this invention to provide an improved blood sampling paraphernalia which allows for the blood cell counts to be made without exposing the technician to contamination from the blood sample.

It is a further object of this invention to provide blood sampling paraphernalia of the character described wherein dimensional tolerances are relaxed while providing the necessary cell layer expansion.

It is an additional object of this invention to provide blood sampling paraphernalia of the character described wherein larger blood samples are tested.

It is still another object of this invention to provide blood sampling paraphernalia of the character described wherein the formation of cell bands after centrifugation, is stabilized and preserved.

It is yet an additional object of this invention to provide blood sampling paraphernalia of the character described wherein improved hydrodynamics during centrifugation is achieved.

These and other objects and advantages of the invention will become more readily apparent from the following description of a preferred embodiment thereof when considered in conjunction with the accompanying drawings, in which:

FIG. 1 is an axial sectional view of a first embodiment of a tube and float assembly formed in accordance with this invention.

FIG. 2 is an axial sectional view of the float;

FIG. 3 is an axial sectional view showing how the assembly can be used to draw a blood sample from a primary blood collecting tube; FIG. 4 is a view similar to FIGS. 1 and 3 but showing the assembly of FIG. 1 after the blood sample has been drawn and centrifuged;

FIG. 5 is a top plan view of a second embodiment of a float and tube for use in the subject invention; and FIG. 6 is a view similar to FIG. 2 of the float used in the second embodiment of the invention.

Referring now to the drawings there is shown in FIG. 1 a preferred embodiment of the blood sampling paraphernalia formed in accordance with this invention. The blood sampling paraphernalia includes a transparent tube 2 formed preferably of glass, and having an integrally closed end 4. A plastic float member 6 is disposed in the tube 2, as are the stain and red cell densifier reagents. An elastomeric plug 10 closes the open end of the tube 2. The tube is preferably about 75 mm long, the same length as a capillary tube, and has a bore diameter of about 4 mm. Its capacity for blood is about 0.9 ml. The float will be about 8 mm in length and about 4 mm in diameter when static in the tube.

The float 6 is a compound structure which has a central through bore 7 into which the white cells and platelets layer out during centrifugation. The bore 7 is preferably about 1.265 mm in diameter so as to achieve the same cell band elongation as with the prior art, when the 0.9 ml tube 2 is used. The float 6 is formed with a core part 9 made from a dimensionally stable transparent plastic, such as a rigid styrene plastic. A sleeve part 11 surrounds the core 9 and is bonded thereto. The sleeve 11 is formed from a pliable transparent plastic such as PVC. The ends of the sleeve 11 are flared, as at 13, and the ends of the bore 7 are also flared as at 15 to allow movement of the blood in the tube 2 during filling and centrifugation.

FIG. 3 shows how the tube 2 can be filled with blood from a primary blood collecting tube 14 by means of a transferring device 16 having a double piercing needle or cannula 18. The transfer device 16 includes an outer shroud 20 with a needle-carrying plug 22 telescoped thereinto. The needle 18 extends into a first well 24 in the plug 22 sized to receive the stoppered end of the blood sampling tube 2. The shroud 20 forms a second well 26 which is sized to receive the stoppered end of the primary blood collecting tube 14. The transfer needle 18 pierces the plug 28 in the tube 14 and also pierces the plug 10 in the sampling tube 2. The low pressure in the tube 2 causes blood to be drawn from the tube 14 through the needle 18 into the tube 2, the flow of blood continuing until the tube 2 is substantially filled. Once filled, the tube 2 is withdrawn from the well 24 and centrifuged. While transferring blood to the testing tube 2 from a collection tube 14 is one way to fill the tube 2, it is readily apparent that the sample could be taken directly from a patient using a needle and the evacuated tube 2.

When the blood enters the tube 2, the reagents 8 will mix with the blood, and the tube 2 will be ready to centrifuge. The tubes 2 are oriented in the centrifuge with the closed end 4 out, so that the red cells will settle in the closed end of the tube 2 and the plasma will be adjacent to the stoppered end of the tube 2 after centrifugation. FIG. 4 shows the condition of the tube 2 and blood after the centrifugation has been completed. The red cells 30 collect in the closed end of the tube 2 and the float 6 becomes embedded in, and projects above the top of the red cell layer. The white cells and platelet layers which make up the buffy coat 32 settle into the axial through bore 7 in the float 10 and the plasma 34 is disposed above the buffy coat and float 10. The tube 2 can thus be placed in a reader instrument of the type generally disclosed in U.S. Pat. Nos. 4,156,570 Wardlaw; or 4,558,947 Wardlaw without disrupting the centrifuged cell band, so that the axial lengths of the white cell and platelet bands can be measured and converted to cell count information by the reader instrument microprocessor.

When the filled tube 2 is subjected to centrifugation forces of 10,000 G, which is the force at which the prior art capillary tubes are centrifuged, the pliable sleeve part 11 of the float 6 radially contract whereby the effective diameter of the float 6 decreases. Thus the float 6 is forced through the blood sample until the float encounters the centrifuged red cell layer which, because of its specific gravity, resists further movement of the float 6. Once this occurs, the float 6 will be stabilized and the sleeve part 11 will expand back outwardly into snug engagement with the tube bore. The tube bore wall may be coated with a silicone lubricant to enhance the slidability of the float 6 in the tube 2.

The embodiment shown in FIGS. 5 and 6 utilizes a float 6 having the channel 7 therein located at the outer side of the float 6 and adjacent to the glass tube.

It will readily appreciated that tubes of this invention can be used to draw blood samples from patients or from blood collecting tubes, and the blood cell measurements can then be made directly in the stoppered, closed tubes without exposing anyone to the possibility of contact with contaminated blood. Thus the blood testing procedure can even be used with patients who are known to have contaminated blood with no danger to the person doing the testing. The dimensional tolerances observed in producing the tubes and floats are relaxed, and the test assemblies have a longer shelf life since the interior of the evacuated tubes is filled with an inert gas. Cell layer band formation is preserved in the through channel during handling of the tube after centrifugation.

Since many changes and variations of the disclosed embodiment of the invention may be made without departing from the inventive concept, it is not intended to limit the invention otherwise than as required by the appended claims.

What is claimed:

1. A blood sampling assembly for measuring buffy coat constituents in a centrifuged sample of blood contained in the assembly without exposing one performing the test to the blood being sampled, said assembly comprising: a transparent tube for holding the sample of blood; an elongated cylindrical transparent float member disposed in said tube, said float member having an outer surface which, during static conditions, closely conforms to the bore of said tube, and said float member being operable to settle into the red blood cell layer of the centrifuged blood sample and said float member having an axially extending passage into which all of the blood sample buffy coat layers out thereby to physically expand the white cell and platelet layers in the buffy coat; an elastomeric stopper sealing one end of said tube; and the interior of said tube having a subatmospheric pressure whereby the blood will be automatically drawn into said tube when said stopper is pierced by a blood sampling needle.

2. The assembly of claim 1 wherein said tube is filled with an inert gas prior to use of the assembly to draw a blood sample.

3. The assembly of claim 1 wherein said float member is a compound structured which includes a dimensionally stable transparent plastic core containing said through bore, and a pliable transparent plastic sleeve extending from one end to the other end of said float and which is bonded to and surrounding said core, said sleeve providing radially contractible means for allowing said float member to freely move through the tube bore when said float member is subjected to centrifugal forces during centrifugation of the blood sample.

4. The assembly of claim 3 wherein said through bore has a diameter of approximately 1.265 mm.

5. The assembly of claim 4 wherein said tube is approximately equal in length to a conventional capillary tube and sized to contain approximately 0.9 ml of blood.

6. The assembly of claim 3 further comprising a lubricant coating on the tube bore wall to enhance the ability of said float member to move in the tube bore.

7. An assembly for performing tests on blood constituents in a centrifuged sample of blood contained in the assembly without exposing one performing the test to the blood being sampled, said assembly comprising: a sealed transparent tube for holding the sample of blood; an elongated transparent cylindrical float disposed in said tube, said float having an axially extending passage for receiving and physically elongating the entirety of any layers of centrifuged blood constituents to be tested during centrifugation of the blood sample to enable measurement of said elongated blood constituent layers in said passage, and said float having an outer surface extending from one end of said float to the other with a diameter which closely conforms to the internal diameter of said tube; and means for contracting said float outer diameter during centrifugation of the assembly and a contained blood sample, whereby said float can freely move axially of said tube during the centrifugation step.

8. The assembly of claim 7 further comprising an elastomeric stopper closing one end of said tube, and wherein said tube is internally evacuated, whereby a blood sample will be automatically drawn into said tube when said stopper is pierced by a blood transferring needle.

9. The assembly of claim 7 wherein said means for contracting is reversible whereby said float outer diameter expands when said float ceases movement through the tube during centrifugation.

10. The assembly of claim 9 wherein said float includes a dimensionally stable core portion through which said passage extends.

11. The assembly of claim 10 wherein said means for contracting is a pliant plastic sleeve on said float extending from one end to the other of said float and surrounding and bonded to said core.

12. The assembly of claim 11 further comprising a lubricant coating on one of said float and the bore of said tube operable to enhance mobility of said float in said tube during centrifugation.

13. The assembly of claim 12 wherein both ends of said through bore are flared to accommodate blood flow through, said passage.

* * * * *